United States Patent [19]

Matsumoto et al.

[11] Patent Number: 5,686,403
[45] Date of Patent: Nov. 11, 1997

[54] CLEANSER COMPOSITION CONTAINING PHOSPHATE ESTER AND ETHER ACETATE SURFACTANTS

[75] Inventors: Chikako Matsumoto; Tadashi Moriyama, both of Wakayama; Takatoshi Kobayashi, Tochigi; Yuichi Hioki, Wakayama, all of Japan

[73] Assignee: Kao Corporation, Tokyo, Japan

[21] Appl. No.: 436,299

[22] PCT Filed: Sep. 22, 1994

[86] PCT No.: PCT/JP94/01567

§ 371 Date: May 19, 1995

§ 102(e) Date: May 19, 1995

[87] PCT Pub. No.: WO95/08615

PCT Pub. Date: Mar. 30, 1995

[30] Foreign Application Priority Data

Sep. 24, 1993 [JP] Japan ................................ 5-238159

[51] Int. Cl.$^6$ ................ C11D 1/37; C11D 1/06; C11D 1/34; C11D 11/00
[52] U.S. Cl. ............. 510/436; 510/122; 510/137; 510/159; 510/467; 510/488; 510/505; 510/506
[58] Field of Search .................. 252/174.16, DIG. 17, 252/DIG. 5, DIG. 13, 174.21, DIG. 1, 171; 510/122, 436, 467, 119, 405, 488, 506, 505, 135–138, 159

[56] References Cited

U.S. PATENT DOCUMENTS

| | | | |
|---|---|---|---|
| 2,183,853 | 12/1939 | Haussmann et al. | 560/198 |
| 4,132,679 | 1/1979 | Tsutsumi et al. | 510/122 |
| 4,435,300 | 3/1984 | Guth et al. | 510/480 |
| 4,486,338 | 12/1984 | Ootani et al. | 510/416 |
| 4,808,239 | 2/1989 | Schafer et al. | 134/42 |
| 5,098,596 | 3/1992 | Balzer | 510/119 |

FOREIGN PATENT DOCUMENTS

| | | |
|---|---|---|
| 0 496 359 | 7/1992 | European Pat. Off. . |
| 1-316309 | 12/1989 | Japan . |
| 3-106999 | 5/1991 | Japan . |
| 3-109498 | 5/1991 | Japan . |
| 3-182598 | 8/1991 | Japan . |
| 2 197 338 | 5/1988 | United Kingdom . |

OTHER PUBLICATIONS

English translation of JP 3–106999, published May 1991.
English translation of JP 3–109498, published May 1991.
English translation of JP 3–182598, published Aug. 1991.
English language abstract of JP–A No. 1–316309, Dec. 21, 1989.
English language abstract of JP–A No. 57–49698, Mar. 23, 1982.

*Primary Examiner*—Ardith Hertzog
*Attorney, Agent, or Firm*—Birch, Stewart, Kolasch & Birch, LLP

[57] ABSTRACT

A cleanser composition comprising an alkylphosphate type surfactant and an ether acetic acid type surfactant represented by the following formula (3):

$$R^4-O-(CH_2CH_2O)_p-CH_2CO_2X^3 \qquad (3)$$

wherein $R^4$ represents an alkyl or alkenyl group having 8 to 18 carbon atoms, $X^3$ represents a hydrogen atom, an alkali metal atom, a triethanolammonium group or an ammonium group, and p represents a number of 3 to 15.

The cleanser composition is excellent in cleansing property of the skin and hair, and low irritant. Further, even when the cleanser composition contains a phosphate salt in a concentration of 30% by weight or above, the viscosity of the composition is not increased and the incorporation of a third component thereinto is easy.

8 Claims, No Drawings

CLEANSER COMPOSITION CONTAINING PHOSPHATE ESTER AND ETHER ACETATE SURFACTANTS

FIELD OF THE INVENTION

The present invention relates to a cleanser composition comprising a phosphate surfactant having an excellent cleansing power and being low irritative to the skin and hair.

The cleanser composition of the present invention is useful as a skin cleanser such as a facial cleanser and a body shampoo or as a hair cleanser such as a shampoo.

Even when the cleanser composition of the present invention contains a high concentration of the phosphate surfactant, it neither causes an increase in viscosity nor gelation.

DESCRIPTION OF THE RELATED ART

Since phosphate surfactants are low irritant to the skin and hair, as compared with soap, alkyl ether sulfates, alkyl sulfates, etc., they are useful as a component of a body cleanser and are used in combination with various anionic and nonionic surfactants (Japanese Patent Publication-A No. 1-316309, etc.).

In the preparation of a cleanser such as a hair shampoo and a body shampoo, a mean which comprises first preparing a surfactant solution containing a high concentration of a surfactant and then adding components, such as a humectant, an oily component, a conditioning component and a powder, and water to the solution to adjust the surfactant concentration to a desired value, is usually employed. However, when the phosphate surfactant is a triethanolamine salt or alkali metal salt thereof and the concentration thereof in the solution is 30% by weight or above, a rapid viscosity increase and gelation are caused to make the handling thereof difficult.

Such a phosphate salt as that described above is prepared by neutralizing a phosphate surfactant having a hydroxyl group. In the neutralization, a large amount of a solvent has been added thereto or a solution containing a low concentration of the phosphate surfactant having a hydroxyl group has been used hitherto in order to keep the viscosity of the solution low after neutralization. The addition of the large amount of the solvent impairs the properties, such as lathering and feeling, of the cleanser to be obtained. While, when a solution containing a low concentration of the phosphate surfactant having a hydroxyl group is used for the neutralization, the neutralized product contains a large amount of water and, therefore, there is a problem that the amount of a third component to be incorporated is limited in the production of the final product by adding the third component thereto.

Accordingly, an object of the present invention is to provide a cleanser composition containing a phosphate surfactant characterized by having a skin-cleansing property and being a low irritant, the viscosity of which composition is not increased even when the concentration of the phosphate salt is 30% by weight or above.

DISCLOSURE OF THE INVENTION

The present inventors have been made extensive investigations under these circumstances. As the result, the inventors have found that a cleanser composition satisfying the above-described requirements can be obtained by using a specific alkyl phosphate surfactant in combination with a specific ether acetic acid surfactant. The present invention has been completed on the basis of this finding.

Thus, the present invention provides a cleanser composition comprising at least 30% by weight, based on the total weight of the composition, of the following component (A), and the following component (B):

component (A): a phosphate surfactant represented by the following formula (1) or a mixture thereof with another phosphate surfactant represented by the following formula (2), wherein the weight ratio of the phosphate surfactant (1) to the phosphate surfactant (2) is 100/0 to 70/30;

and

wherein $R^1$, $R^2$ and $R^3$ each represents a linear or branched alkyl or alkenyl group having 8 to 18 carbon atoms, $X^1$, $X^2$ and $Y$ each represents a hydrogen atom, an alkali metal atom, a triethanolammonium group or an ammonium group; and component (B): an ether acetic acid surfactant represented by the following formula (3);

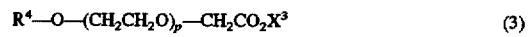

wherein $R^4$ represents a linear or branched alkyl or alkenyl group having 8 to 18 carbon atoms, $X^3$ represents a hydrogen atom, an alkali metal atom, a triethanolammonium group or an ammonium group, and p represents a number of 3 to 15.

Further, the present invention provides a process for preventing an increase in the viscosity of a solution containing the above component (A) in an amount of 30% by weight or above, which comprises adding the above component (B).

Furthermore, the present invention further provides a use of the above component (B) for preventing an increase in the viscosity of a solution containing the above component (A) in an amount of 30% by weight or above.

Among the phosphate surfactants to be used as component (A) in the present invention, those represented by the formula (1) wherein $R^1$ represents an alkyl group having 10 to 16 carbon atoms, particularly 12 to 14 carbon atoms, and those represented by the formula (2) wherein $R^2$ and $R^3$ each represents an alkyl group having 10 to 16 carbon atoms, particularly 12 to 14 carbon atoms, are preferred. In addition, those represented by the formula (1) wherein $X^1$ and $Y$ each represents an alkali metal atom, particularly potassium atom from the viewpoint of the solubility in water, and those represented by the formula (2) wherein $X^2$ represents an alkali metal atom, particularly potassium atom from the viewpoint of solubility in water, are preferred.

Component (A) comprises the phosphate surfactant represented by the formula (1) (hereinafter referred to as the monoalkyl phosphate (1)) or a mixture thereof with a phosphate surfactant represented by the formula (2) ([hereinafter referred to as the dialkyl phosphate (2)).

The monoalkyl phosphate (1) content of the component (A) is at least 70% by weight, preferably at least 80% by weight. When the monoalkyl phosphate (1) is below 70% by weight, the obtained cleanser composition has poor lathering property and cleansing power unfavorably.

The cleanser composition of the present invention contains the component (A) in an amount of 30% by weight or above, preferably 30 to 60% by weight and still more preferably 35 to 50% by weight, based on the total weight of the composition.

Among the ether acetic acid surfactants to be used as component (B) in the present invention, those represented by the formula (3) wherein $R^4$ represents an alkyl or alkenyl group having 10 to 16, particularly 12 to 14 carbon atoms, are preferred. p in the formula (3) represents the average addition molar number of ethylene oxide, which must be 3 to 15, preferably 8 to 12. When p exceeds 15, the lathering power of the surfactant becomes poor. While, when it is below 3, the surfactant cannot prevent an increase in the viscosity of the solution containing a high concentration of the component (A). $X^3$ in the formula (3) is preferably an alkali metal atom, particularly potassium atom.

Specific examples of the ether acetic acid surfactants represented by the formula (3) [hereinafter referred to as the ether acetic acid surfactant (8)] include polyoxyethylene(10) lauryl ether acetic acid, polyoxyethylene(8) myristyl ether acetic acid, and alkali metal salts, triethanolamine salts and ammonium salts of them.

The component (B) is preferably an ether acetic acid surfactant (3) having a degree of neutralization of 60 to 120%.

The cleanser composition of the present invention contains the component (B) in an amount of preferably 0.6 to 20% by weight, still more preferably 2 to 10% by weight, based on the total weight of the composition.

The weight ratio of the component (A) to the component (B), i.e., (A)/(B), is preferably 75/25 to 98/2, particularly 85/15 to 95/5. When the ratio is below 75/25, the cleanser composition has poor lathering power and cleansing power. While, when it exceeds 98/2, it is difficult to incorporate the component (A) into the solution so as to obtain a concentration of as high as 30% by weight or above.

When the cleanser composition of the present invention contains the component (A) in an amount of 35% by weight or above, this composition preferably contains, further, a polyhydric alcohol.

Examples of the polyhydric alcohols include ethylene glycol, diethylene glycol, propylene glycol, dipropylene glycol, glycerol, diglycerol and triglycerol. Among them, propylene glycol, ethylene glycol and glycerol are preferred.

In the cleanser composition of the present invention, the weight ratio of the sum total of the components (A) and (B) to the polyhydric alcohol, i.e. [(A)+(B)]/polyhydric alcohol, is preferably 80/20 to 99/1, still more preferably 85/15 to 98/2, and particularly preferably 90/10 to 96/4. When the ratio is below 80/20, the obtained cleanser composition are poor in lathering and cleansing properties, though the concentration of the component (A) in the cleanser composition can be increased. While, when it exceeds 99/1, it is impossible to obtain the solution containing the component (A) in a concentration of 35% by weight or above.

One embodiment of the cleanser composition according to the present invention is a base for preparing a low-viscosity cleanser, which contains the components (A) and (B) as the essential components and in which the amount of the component (A) is at least 30% by weight and that of the component (B) is preferably 0.6 to 20% by weight, still more preferably 2 to 10% by weight. Another embodiment is a cleanser composition containing various optional components in addition to the essential components.

Even when the cleanser composition of the present invention contains the component (A) in an amount of 30% by weight or above (preferably 30 to 60% by weight, still more preferably 30 to 50% by weight and particularly preferably 35 to 50% by weight) based on the total weight of the composition, it causes neither viscosity increase nor gelation and it exhibits an excellent fluidity at room temperature (25° C.). In other words, such a cleanser composition is maintained in the viscosity of 10,000 to 50 cps, preferably 8,000 to 50 cps and still more preferably 5,000 to 50 cps as determined with a Brookfield viscometer at 30° C. The viscosity was determined with the Brookfield viscometer by suitably selecting the rotor and the number of revolutions thereof depending on the viscosity of the liquid to be tested as given in Table 1.

TABLE 1

| Determination conditions | | |
|---|---|---|
| Determination viscosity (cps) | Rotor No. | No. of revolutions |
| 5–300 | 1 | 12 |
|  | 2 | 60 |
| 300–800 | 1 | 6 |
|  | 2 | 30 |
| 800–2000 | 2 | 12 |
|  | 3 | 60 |
| 2000–4000 | 2 | 6 |
|  | 3 | 30 |
| 4000–10000 | 3 | 12 |
|  | 3 | 6 |
| 10000–18000 | 4 | 30 |
| 18000–40000 | 4 | 12 |

The cleanser composition of the present invention is also useful as a skin cleanser such as a facial cleanser and a body shampoo or as a hair cleanser such as a shampoo. Such cleansing products are usually prepared by adding various optional components depending on the use to the cleanser composition of the present invention comprising the components (A) and (B) and, if necessary, the polyhydric alcohol, wherein the concentration of the component (A) is at least 30% by weight.

Examples of the optional components contained in the cleanser composition of the present invention include anionic surfactants, nonionic surfactants, amphoteric surfactants, cationic surfactants and conditioning components which are usually contained in a skin cleanser or a hair cleanser.

Examples of the anionic surfactants include fatty acid salts, alkylsulfates, polyoxyalkylene alkyl ether sulfates, sulfosuccinic acid surfactants, sulfosuccinate surfactants, polyoxyalkylene alkylamide ether sulfates, monoglyceride sulfates, olefinsulfonates, alkanesulfonates, acylated isethionates, acylated amino acid salts and polyoxyalkylene alkyl ether phosphates; and examples of the nonionic surfactants include alkyl polyglycoxides, sucrose/fatty acid esters, polyglycerol/fatty acid esters, polyoxyalkylene alkyl ethers, fatty acid alkanolamides, alkylamine oxides and fatty acid/polyhydric alcohol esters. Examples of the cationic surfactants include linear or branched, mono- or di(long-chain alkyl) quaternary ammonium salts and mono- or di(long-chain alkyl) tertiary amines; and examples of the amphoteric surfactants include amidoamino acid surfactants, carbobetaine surfactants, sulfobetaine surfactants, amidosulfobetaine surfactants, imidazolium betainesurfactants, amino acid betaine surfactants, phosphobetaine surfactants and the like.

Examples of the conditioning components include oils such as higher alcohols, silicones and silicone derivatives, lanolin, squalene, hydrocarbons, protein derivatives and fatty acid esters of polyethylene glycols, and cationic polymers such as cationized cellulose, cationized guar gum and Merquat 550 (a product of Merck).

The cleanser composition of the present invention may further contain other components usually employed in a cleanser composition, such as water-soluble polymers, e.g. methylcellulose, hydroxyethylcellulose, carboxyvinyl polymer and xanthan gum; viscosity modifiers, e.g. polyoxyalkylene sorbitan esters, polyoxyethylene glycol distearates and ethanol; chelating agents, e.g. ethylenediaminetetraacetic acid (EDTA) and phosphonic acid salts; antiseptics, e.g. methylparaben and butylparaben; active ingredients, e.g. vitamins and percursors thereof; animal and vegetable extracts or derivatives thereof, e.g. lecithin and gelatin; finely pulverized polymers, e.g. nylons and polyethylenes; antiphlogistics, e.g. dipotassium glycyrrhizate; germicides and antidandruff agents, e.g. Triclosan, Triclorocarban, Octopirox and zinc pyrithione; antioxidants, e.g. dibutylhydroxy-toluene; pearling agents; ultraviolet absorbers; pH regulators; colorants; fragrances; and water so long as the effect of the present invention is not impaired.

The cleanser composition of the present invention is not only the base for preparing a low-viscosity cleanser which contains the components (A) and (B) as the essential components and in which the concentration of the component (A) is at least 30% by weight, but also a composition which is prepared by adding various optional components described above to the base and contains at least 30% by weight, based on the total weight of the composition, of the component (A). Usually, the former is used as the base for preparing a cleanser, and the latter is used as various final cleansing products. Every cleanser composition of the present invention is preferably in the form of a liquid such as an emulsion, solution and suspension.

The cleanser composition of the present invention is excellent in cleansing property to the skin and hair and low irritant. The cleanser composition of the present invention has a low viscosity even when it has a surfactant concentration of 30% by weight or above.

EXAMPLES

The present invention will be described hereinafter by referring Examples, though the present invention is not limited to these Examples only.

Example

Cleanser compositions each having the composition listed in Tables 2 and 3 were prepared by an ordinary process. The viscosity, quantity of the formed foams and cleansing rate of the cleanser compositions were determined by the methods which will be described below, and also the feeling realized during the cleansing with them was evaluated by an organoleptic test. All the determination and evaluation were conducted in a solution at pH 7.

The results are given in Tables 2 and 3.

<Viscosity>

The viscosity of the present-invention-product or the comparative product itself, and that of the solution obtained by diluting the product with water resulting a concentration of the component (A) of by weight, was determined with a Brookfield viscometer at a determination temperature of 30° C.

<Quantity of the Formed Foams>

Each detergent composition and lanolin were added to water to prepare a mixture having a total surfactant concentration of 1% by weight, a lanolin concentration of 0.5% by weight and the total amount of 100 g. The mixture thus obtained was stirred by the reverse revolution stirring method at 40° C. for 5 min, and the quantity of the foams was determined 30 sec after the termination of the stirring.

<Cleansing Rate>

0.4 ml of a chloroform solution containing 7% by weight of lanolin and 0.005% by weight of Sudan III (a product of Wako Pure Chemical Industries, Ltd.) was uniformly applied to a wool muslin cloth having a size of 5×5 cm, and the cloth thus obtained was dried to give a stained cloth. The stained cloth was washed by stirring in 40 ml of an aqueous cleanser solution having the cleanser composition concentration of 2% by weight at 40° C. for 10 min, thoroughly rinsed in running water, and dried. The reflectance of each stained cloth before and after the washing and an unstained cloth was determined to calculate the cleansing rate according to the following formula:

$$\text{Cleansing rate (\%)} = \frac{\left[\begin{array}{c}\text{reflectance of}\\\text{stained cloth}\\\text{after washing}\end{array}\right] - \left[\begin{array}{c}\text{reflectance of}\\\text{stained cloth}\\\text{before washing}\end{array}\right]}{\left[\begin{array}{c}\text{reflectance of}\\\text{unstained}\\\text{cloth}\end{array}\right] - \left[\begin{array}{c}\text{reflectance of}\\\text{stained cloth}\\\text{before washing}\end{array}\right]}$$

In the Tables 2 and 3, the description in the column of the cleansing rate means as follows:

⊚: cleansing rate of 85% or above,

○: cleansing rate of 70% to less than 85%,

△: cleansing rate of 60% to less than 70%, and x: cleansing rate of less than 60%.

<Feeling in the Course of Washing>

A hand-washing test was conducted with each cleanser composition by 10 specialized panelists, and the feeling of the hands during washing was evaluated according to the following criteria:

○: good feeling,

△: slightly bad feeling, and x: bad feeling.

TABLE 2

|  |  | Present-invention-product | | | | | | |
|---|---|---|---|---|---|---|---|---|
|  |  | 1 | 2 | 3 | 4 | 5 | 6 | 7 |
| Component (A) | K salt of lauryl phosphate/K salt of dilauryl phosphate (monolauryl/dilauryl = 95/5) | 40 | 40 | — | — | 40 | 40 | 40 |
|  | triethanolamine salt of lauryl phosphate/triethanolamine salt of | — | — | — | — | — | — | — |

TABLE 2-continued

| | | Present-invention-product | | | | | | |
|---|---|---|---|---|---|---|---|---|
| | | 1 | 2 | 3 | 4 | 5 | 6 | 7 |
| | dilauryl phosphate (monolauryl/dilauryl = 95/5) | | | | | | | |
| | K salt of lauryl phosphate/K salt of dilauryl phosphate (monolauryl/dilauryl = 80/20) | — | — | 40 | 40 | — | — | — |
| | triethanolamine salt of lauryl phosphate/triethanolamine salt of dilauryl phosphate (monolauryl/dilauryl = 80/20) | — | — | — | — | — | — | — |
| Component (B) | K salt of polyoxyethylene alkyl ether acetate (alkyl groups: $C_{12}/C_{14}$ =75/25, average addition molar number of EO: 10) | 8 | 8 | 8 | 8 | 8 | 8 | 8 |
| Propylene glycol | | — | 3.5 | — | 3.5 | 2.0 | 1.0 | 3.5 |
| Water | | balance | balance | balance | balance | balance | balance | balance |
| Surfactant concn. [(A) + (B)] (% by wt.) | | 48 | 48 | 48 | 48 | 48 | 48 | 43 |
| Viscosity (cps) | | 3680 | 2900 | 4320 | 3200 | 3315 | 3490 | 3510 |
| Viscosity (cps) (aq. soln. having a surfactant concn. of 35% by wt.) | | 700 | 580 | 820 | 610 | 620 | 650 | 695 |
| Cleansing rate (%) | | ⊚ | ⊚ | ○ | ○ | ⊚ | ⊚ | ⊚ |
| Quantity of the formed foams (ml) | | 90 | 87 | 78 | 74 | 86 | 88 | 87 |
| Feeling during cleansing | | ○ | ○ | ○ | ○ | ○ | ○ | ○ |

TABLE 3

| | | Present-invention-product | | Comp. product | | | |
|---|---|---|---|---|---|---|---|
| | | 8 | 9 | 1 | 2 | 3 | 4 |
| Component (A) | K salt of lauryl phosphate/K salt of dilauryl phosphate (monolauryl/dilauryl = 95/5) | — | — | 40 | 40 | — | — |
| | triethanolamine salt of lauryl phosphate/triethanolamine salt of dilauryl phosphate (monolauryl/dilauryl = 95/5) | 40 | — | — | — | — | 40 |
| | K salt of lauryl phosphate/K salt of dilauryl phosphate (monolauryl/dilauryl = 80/20) | — | — | — | — | 40 | — |
| | triethanolamine salt of lauryl phosphate/triethanolamine salt of dilauryl phosphate (monolauryl/dilauryl = 80/20) | — | 40 | — | — | — | — |
| Component (B) | K salt of polyoxyethylene alkyl ether acetate (alkyl groups: $C_{12}/C_{14}$ = 75/25, average addition molar number of EO: 10) | 5 | 8 | — | — | — | — |
| Propylene glycol | | 3.5 | 3.5 | — | 3.5 | — | — |
| Water | | balance | balance | balance | balance | balance | balance |
| Surfactant concn. [(A) + (B)] (% by wt.) | | 45 | 48 | 40 | 40 | 40 | 40 |
| Viscosity (cps) | | 3000 | 3035 | gelation | gelation | gelation | gelation |
| Viscosity (cps) (aq. soln. having a surfactant concn. of 35% by wt.) | | 580 | 600 | gelation | 25000 | 20000 | gelation |
| Cleansing rate (%) | | ⊚ | ⊚ | ○ | ○ | △ | ○ |
| Quantity of the formed foams (ml) | | 72 | 69 | 78 | 65 | 59 | 63 |
| Feeling during cleansing | | ○ | ○ | △ | △ | × | ○ |

Formulation Examples

Body shampoos, face cleansers and hair shampoos of Formulation Examples 1 to 7 were prepared by using the products of the present invention listed in Tables 2 and 3. The pH was adjusted with citric acid and/or an aqueous NaOH solution. The body shampoos, face cleansers and hair shampoos thus obtained were each low irritant and excellent in cleansing power and feeling of the skin and hair after cleansing.

| | (% by wt.) |
|---|---|
| Formulation Example 1 (body shampoo, pH 7.7) | |
| 1. Invention product 5 | 30.0 |
| 2. laurylhydroxysulfobetaine | 5.0 |
| 3. sodium N-lauroyl-N'-carboxymethyl-N'-(2-hydroxyethyl)ethylenediamine | 3.0 |

-continued

| | (% by wt.) |
|---|---|
| 4. coconut oil fatty acid diethanolamide | 5.0 |
| 5. polyoxyethylene (140) sorbitan diisostearate | 0.5 |
| 6. paraben | 0.2 |
| 7. dibutylhydroxytoluene | 0.2 |
| 8. colorant | trace |
| 9. fragrance | 0.3 |
| 10. purified water | balance |
| Formulation Example 2 (deodorant body shampoo, pH 7.2) | |
| 1. Invention product 5 | 30.0 |
| 2. sodium polyoxyethylene(2.0) lauryl ether phosphate | 4.0 |
| 3. sodium lauroylglutamate | 3.0 |
| 4. coconut oil fatty acid monoethanolamide | 2.0 |
| 5. zinc stearate | 1.0 |
| 6. ethylene glycol distearate | 1.0 |
| 7. Triclosan | 0.3 |
| 8. paraben | 0.2 |
| 9. colorant | trace |
| 10. fragrance | 0.3 |
| 11. purified water | balance |
| Formulation Example 3 (body shampoo, pH 6.7) | |
| 1. Invention product 6 | 32.0 |
| 2. lauryl polyglycoside | 3.0 |
| 3. disodium polyoxyethyene(3.0) lauryl ether sulfosuccinate | 2.0 |
| 4. lauryldimethylaminoacetic acid betaine | 2.0 |
| 5. cationized cellulose (Polymer JR 30 M; a product of UCC) | 0.2 |
| 6. paraben | 0.2 |
| 7. colorant | trace |
| 8. fragrance | 0.3 |
| 9. purified water | balance |
| Formulation Example 4 (antidandruff shampoo, pH 7.4) | |
| 1. Invention product 6 | 10.0 |
| 2. sodium olefinsulfonate (carbon atom number of the hydrocarbon group: 12 to 18) | 7.0 |
| 3. sodium polyoxyethylene(2.0) coconut oil fatty acid monoethanolamide sulfate | 5.0 |
| 4. lauryldimethylamine oxide | 3.0 |
| 5. polyether-modified silicone (KF 352 (A); a product of Shin-Etsu Chemical Co., Ltd.) | 0.4 |
| 6. stearyltrimethylammonium chloride | 0.1 |
| 7. hydroxyethylcellulose | 0.3 |
| 8. Octopirox | 0.3 |
| 9. EDTA | 0.2 |
| 10. paraben | 0.2 |
| 11. colorant | trace |
| 12. fragrance | 0.1 |
| 13. purified water | balance |
| Formulation Example 5 (scrubbing body shampoo, pH 7.8) | |
| 1. Invention product 6 | 32.0 |
| 2. potassium laurate | 7.0 |
| 3. coconut oil fatty acid amide propylbetaine | 3.0 |
| 4. glycerol | 3.0 |
| 5. nylon powder | 0.1 |
| 6. carboxyvinyl monomer (Carbopol 941; a product of B.F. Goodrich) | 0.2 |
| 7. colorant | trace |
| 8. fragrance | 0.3 |
| 9. purified water | balance |

| | (% by wt.) |
|---|---|
| Formulation Example 6 (face cleanser, pH 7.4) | |
| 1. Invention product 9 | 40.0 |
| 2. triethanolammonium laurate | 3.0 |
| 3. sodium lauroylmethyltaurine | 2.0 |
| 4. polyethylene glycol 60000 | 4.0 |
| 5. lauroyl sarcosinate | 6.0 |
| 6. sodium chloride | 10.0 |
| 7. paraben | 0.2 |
| 8. colorant | trace |
| 9. fragrance | 0.3 |
| 10. purified water | balance |

We claim:

1. A cleanser composition comprising at least 30% by weight, based on the total weight of the composition, of the following component (A): a phosphate surfactant represented by the following formula (1) or a mixture thereof with another phosphate surfactant represented by the following formula (2), wherein the weight ratio of the phosphate surfactant (1) to the phosphate surfactant (2) is 100/0 to 70/30;

$$R^1-O-\underset{\underset{OX^1}{|}}{\overset{\overset{O}{\|}}{P}}-OY \quad (1)$$

and $$\underset{R^3O}{\overset{R^2O}{\diagdown}}\overset{\overset{O}{\|}}{P}\underset{OX^2}{\diagup} \quad (2)$$

wherein $R^1$, $R^2$ and $R^3$ each represents a linear or branched alkyl or alkenyl group having 8 to 18 carbon atoms, $X^1$, $X^2$ and Y each represents a hydrogen atom, an alkali metal atom, a triethanolammonium group or an ammonium group; and the following component (B): an ether acetic acid surfactant represented by the following formula (3);

$$R^4-O-(CH_2CH_2O)_p-CH_2CO_2X^3 \quad (3)$$

wherein $R^4$ represents a linear or branched alkyl or alkenyl group having 8 to 18 carbon atoms, $X^3$ represents a hydrogen atom, an alkali metal atom, a triethanolammonium group or an ammonium group, and p represents a number of 3 to 15; wherein the weight ratio of the component (A) to the component (B) is 75/25 to 98/2 and wherein component (B) prevents an increase in viscosity of said composition.

2. The cleanser composition according to claim 1, wherein $X^1$, $X^2$, $X^3$ and Y each represents an alkali metal atom.

3. The cleanser composition according to claim 1, which contains the component (A) in an amount of 30 to 60% by weight based on the total weight of the composition.

4. A cleanser composition comprising at least 30% by weight, based on the total weight of the composition, of the following component (A): a phosphate surfactant represented by the following formula (1) or a mixture thereof with another phosphate surfactant represented by the following formula (2), wherein the weight ratio of the phosphate surfactant (1) to the phosphate surfactant (2) is 100/0 to 70/30;

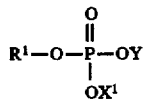 (1)

and

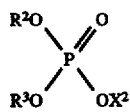 (2)

wherein $R^1$, $R^2$ and $R^3$ each represents a linear or branched alkyl or alkenyl group having 8 to 18 carbon atoms, $X^1$, $X^2$ and Y each represents a hydrogen atom, an alkali metal atom, a triethanolammonium group or an ammonium group; and the following component (B): an ether acetic acid surfactant represented by the following formula (3);

$$R^4-O-(CH_2CH_2O)_p-CH_2CO_2X^3 \quad (3)$$

wherein $R^4$ represents a linear or branched alkyl or alkenyl group having 8 to 18 carbon atoms, $X^3$ represents a hydrogen atom, an alkali metal atom, a triethanolammonium group or an ammonium group, and p represents a number of 3 to 15; wherein the weight ratio of the component (A) to the component (B) is 75/25 to 98/2 wherein component (B) prevents an increase in viscosity of said composition; and component (C): a polyhydric alcohol; and
wherein the weight ratio of the sum total of the components (A) and (B) to (C) is 80/20 to 99/1.

5. The cleanser composition according to claim 4 wherein component (A) is present in an amount of 30 to 60 wt. % based on the weight of the composition.

6. The cleanser composition according to claim 4, wherein the weight ratio of the sum total of the components (A) and (B) to the polyhydric alcohol is 80/20 to 99/1.

7. The cleanser composition according to claim 4, wherein the weight ratio of the sum total of the components (A) and (B) to the polyhydric alcohol is 90/10 to 96/4.

8. A process for preventing an increase in the viscosity of a solution containing the following component (A) in an amount of 30% by weight or above, which comprises adding the following component (B) to said solution:

component (A): a phosphate surfactant represented by the following formula (1) or a mixture thereof with another phosphate surfactant represented by the following formula (2), wherein the weight ratio of the phosphate surfactant (1) to the phosphate surfactant (2) is 100/0 to 70/30;

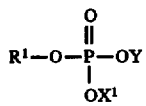 (1)

and

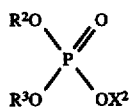 (2)

wherein $R^1$, $R^2$ and $R^3$ each represents a linear or branched alkyl or alkenyl group having 8 to 18 carbon atoms, $X^1$, $X^2$ and Y each represents a hydrogen atom, an alkali metal atom, a triethanolammonium group or an ammonium group;

component (B): an ether acetic acid surfactant represented by the following formula (3);

$$R^4-O-(CH_2CH_2O)_p-CH_2CO_2X^3 \quad (3)$$

wherein $R^4$ represents a linear or branched alkyl or alkenyl group having 8 to 18 carbon atoms, $X^3$ represents a hydrogen atom, an alkali metal atom, a triethanolammonium group or an ammonium group, and p represents a number of 3 to 15.

* * * * *